United States Patent [19]

Olson et al.

[11] Patent Number: 4,565,969

[45] Date of Patent: Jan. 21, 1986

[54] SATURATION CURRENT INCIPIENT SOOT DETECTOR

[75] Inventors: Douglas B. Olson, Lawrenceville; Hartwell F. Calcote, Princeton, both of N.J.

[73] Assignee: AeroChem Research Laboratories, Inc., Princton, N.J.

[21] Appl. No.: 489,714

[22] Filed: Apr. 29, 1983

[51] Int. Cl.[4] ............................................. G01N 27/62
[52] U.S. Cl. ..................... 324/468; 436/154
[58] Field of Search ............... 324/452, 454, 457, 458, 324/459, 464, 468; 340/628, 629; 436/154

[56] References Cited

U.S. PATENT DOCUMENTS

| | | | |
|---|---|---|---|
| 3,340,014 | 9/1967 | Neal et al. | 23/254 |
| 3,469,398 | 9/1969 | Schafer | 324/464 |
| 3,541,431 | 11/1970 | Maise et al. | 324/464 |
| 3,585,003 | 6/1971 | Scolnick | 436/154 |
| 3,589,869 | 6/1971 | Scolnick | 324/464 |
| 3,615,237 | 10/1971 | Speakman | 436/154 |
| 3,814,583 | 6/1974 | Miller et al. | 436/154 |
| 4,176,311 | 11/1979 | Davis | 324/468 |

Primary Examiner—Ernest F. Karlsen
Assistant Examiner—Kevin D. O'Shea
Attorney, Agent, or Firm—Richard C. Woodbridge

[57] ABSTRACT

A method and apparatus are employed to detect the onset of soot or smoke formation in a flame exhaust. A pair of oppositely charged electrodes are placed in a flame located where soot formation is likely to occur. Varying voltages are applied across the electrodes and the limiting current, as the voltage is increased, called the saturation current, is measured. Generally, the saturation current decreases for higher fuel-to-air ratios in non-sooting flames. When the threshold for soot formation is approached, a definite saturation current is no longer observed and the current through the electrodes increases rapidly with increasing applied electrode voltage. The detection of the rapidly increasing current during sooting conditions is indicative of the formation of the soot itself. The method and apparatus can be employed to detect the onset of soot in various flames including, but not limited to, laminar premixed flames, laminar diffusion flames, turbulent premixed or diffusion flames, or otherwise generated high temperature gas flows. The method and apparatus can be employed in practical embodiments for the detection of the onset of soot formation in oil burners, gas burners and jet engines and the like.

21 Claims, 19 Drawing Figures

SATURATION CURRENT INCIPIENT SOOT DETECTOR

GOVERNMENT CONTRACTS

Research performed by the applicants was the subject of government (N.A.S.A.) contracts No. NAS 3-22131 and NAS 3-23161.

BACKGROUND OF THE INVENTION

1. Field of the Invention

This invention relates to a method and apparatus for detecting the threshold of soot formation in a flame or other combustion device by measuring the saturation current through an electrostatic probe in the vicinity of the combustor.

2. Description of the Prior Art

It is well known to use electrical probes to monitor various conditions of combustion. The following U.S. patents are typical of prior art inventions in which a combustion process is monitored with an electrical probe: U.S. Pat. Nos. 3,340,014; 3,469,398; 3,541,431 and 3,589,869. Insofar as applicant is aware, none of the prior art recognizes the dramatic change in saturation current which occurs at the inception of soot formation in a flame. It was in the context of the foregoing prior art that the invention arose.

SUMMARY OF THE INVENTION

Briefly described, the invention comprises a method and apparatus for determining the incipient threshold for soot formation in a combustor. The detection of soot is based upon the observation that saturation current through electrodes exposed to exhaust gases increases when soot particles are contained in the gases. When the current to the electrodes is measured at several increasing voltages on the electrodes, a limiting current, called a saturation current, is observed for a non-sooting flow. This saturation current typically decreases for higher fuel-to-air ratios in non-sooting flames. However, when the threshold for soot formation is approached, a definite limiting plateau in the current vs. voltage curve is no longer observed and the current increases rapidly with increasing electrode voltage. This increase in probe current at soot threshold is observed in several combustor types and is sensitive to small amounts of soot production.

The invention relies upon the phenomenon of thermal ionization of soot particles where at high temperatures a certain portion of the particles are charged positively in a process which also releases negatively charged electrons into the flow. When no particles are present in the flow only a low concentration of ionized species are present downstream from the main reaction zone of the flame. Thus only a small probe current is measured. When soot particles are present in the high temperature flow, thermal ionization processes may not only create an increased concentration of charged particles and electrons, but also replace them as they are removed to the probe electrodes. Since more charged species are produced as others are removed, the current to the probe increases without limit over a certain range of conditions. Thus the saturation probe current observed with and without soot particles in the flow are different and can be used as a sensitive incipient soot detector. The phenomenon is accurately detectable in laminar premixed flames. The phenomenon is somewhat more difficult to detect in laminar diffusion flames or turbulent flames. Accordingly, the invention has a fairly wide range of practical applications, including, but not limited to, the detection of the onset of soot formation in oil burners, gas burners, jet engines, and the like.

The invention can be further understood with reference to the following drawings and detailed description.

DETAILED DESCRIPTION OF THE INVENTION

During the course of this description like numbers will be used to indicate the same elements according to the different drawings which illustrate the apparatus and method.

The simplest and most commonly used diagnostic tools for characterizing charged species in combustion systems are electrostatic probes. Detailed quantitative measurements of positive ion concentrations, electron concentrations, and electron temperatures have been made using Langmuir probes in various flames and plasmas. It is also possible to use probes external to the flame where ions are transported by an electrostatic field and the probe is sufficiently large that all of the ions produced in the given volume are collected. As the voltage on an external probe is increased, more and more ions are removed from the flame thus increasing the measured current. This increase in current with applied potential continues until the loss of ions to the probe completely dominates ion electron recombination. At this point the current no longer increases with the voltage since the ions are removed as soon as they are produced. This is referred to as a saturation current and is found to be virtually independent of the electrode spacing. Saturation current measurements are usually insensitive to the identity of the ions in the flame. However, if the flame ions are produced by thermal ionization rather than chemi-ionization, a distinct saturation current is not established. Instead thermal ionization reactions can shift equilibrium as the charged products are removed to the probe and therefore these reactions produce more ions. In other words, a thermal ionization process is not characterized by a definite limiting rate of ion production as in a chemi-ionization process.

Figure 1:
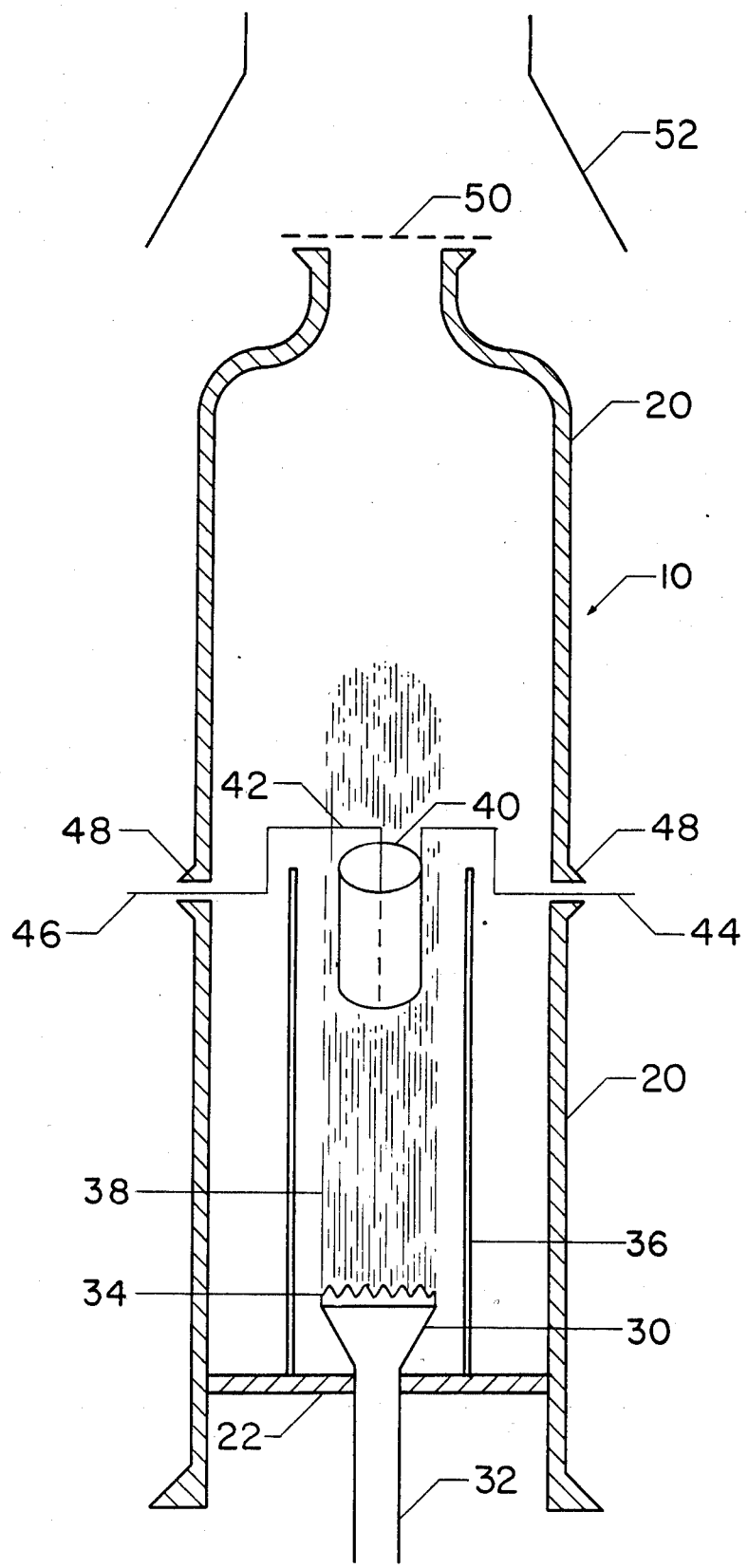
FIG. 1 is a view of the preferred embodiment of the invention as applied to laboratory flames.
Figure 2:
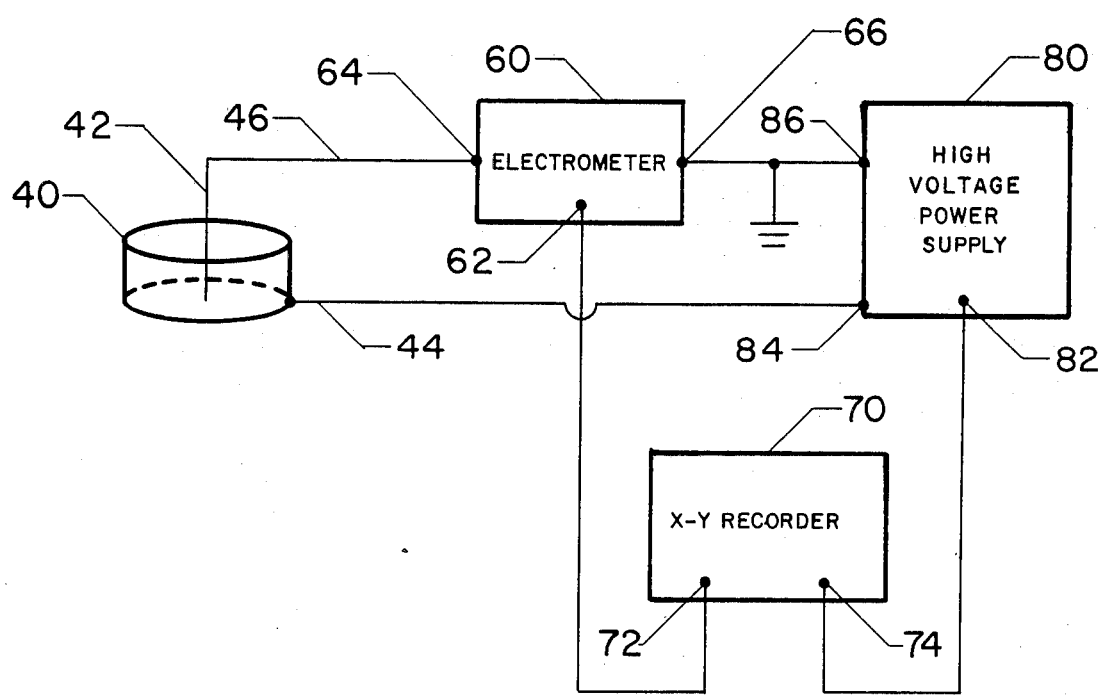
FIG. 2 is a schematic illustration showing the associated electronic components necessary for measuring current and applying voltage to the probe.
Figure 3:
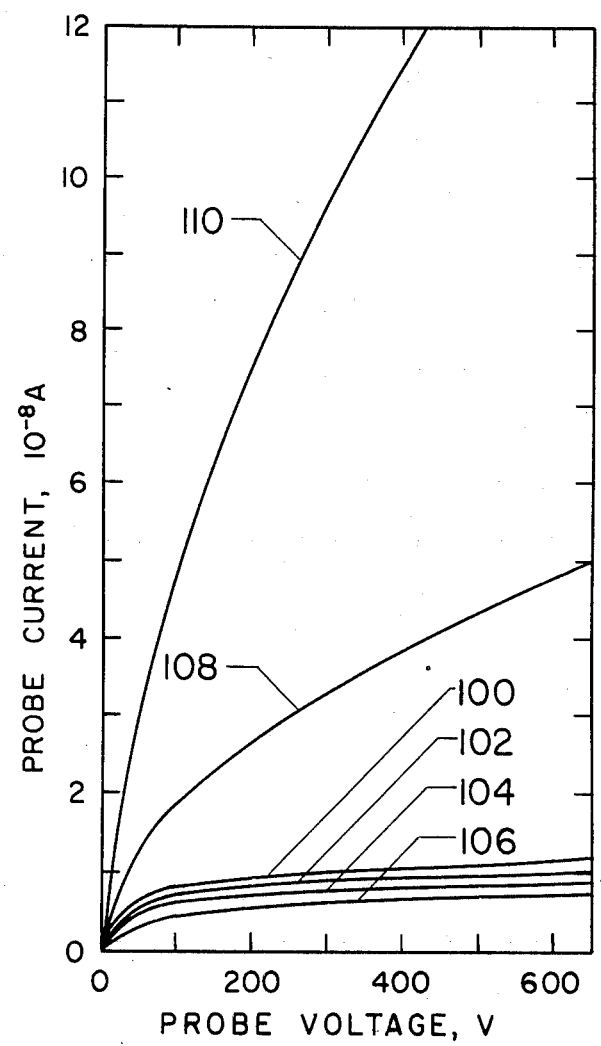
FIG. 3 shows probe current vs. probe voltage curves obtained in a premixed flame.

The technique on which this invention is based uses this difference in saturation current characteristics to discriminate between normal flame chemi-ions and charged soot species which are thermally ionized. As discussed below, the probe technique has been found to be a very sensitive indicator of the threshold at which soot is first formed in the flame. The specific invention covered by this application can be best understood by relating it to the preferred embodiment illustrated in FIGS. 1 and 2. In FIG. 1 the apparatus 10, includes a glass housing 20, in which a hydrocarbon flame 34 is burned upon burner 30. Burner 30 consists of a common laboratory Meker burner which stabilizes a premixed hydrocabon-air flame 34. The fuel and air mixture flow into the burner through tube 32. The base of the housing 20 is enclosed with a metal disk 22. The flame 34 and exhaust gases 38 are surrounded by a Vycor ® glass chimney 36. Vycor ® is a registered trademark of Corning Glass, Corning, N.Y. The probe anode and cathode 40, 42 respectively are located at the top of the chimney with electrical connections made using wires 44, 46, through sealed holes in the glass container 48. At the top of the housing 20 a wire screen 50 prevents air from entering the apparatus at the top of the chimney. The exhaust gases are removed from the laboratory using a vent 52. The probe electrodes 40, 42 can be located at several different distances above burner 30. FIG. 2 shows the electrical connections for measuring probe currents at adjustable probe bias voltages. The high voltage power supply 80 supplies an adjustable 0–3000 volt potential to the anode 40 by connecting a wire from junction 84 to probe junction 44. A sensitive electrometer 60 measures the current to the cathode 42 through wire connections 46 to 64 and 66 to 86. The electrometer is operated at near ground potential. X-Y recorder 70 creates curves in which the high voltage power supply voltage is represented as the X axis and the current measured by the electrometer 60 is represented as the Y axis through inputs 72 and 74. In this way continuous measurements of current at adjustable voltages can be conveniently made and recorded onto chart paper as shown in example in FIG. 3. The flame system in this example was propane-air with each line in the chart representing a different fuel to air ratio. This fuel to air ratio is specified by the equivalence ratio which is defined as the actual fuel to air ratio being used divided by the fuel to air ratio for stoichiometric combustion assuming complete combustion to water and carbon dioxide. An equivalance ratio of exactly 1 corresponds to the stoichiometric fuel to air mixture. Equivalence ratios greater than 1 represent mixtures with excess fuel. Lines 100–106 represent flames with equivalance ratios of 1.5, 1.6, 1.7, and 1.8. Lines 108 and 110 represent flames with equivalence ratios of 1.85 and 1.9. Soot is first observed in this flame at an equivalence ratio of 1.82, thus lines 100–106 represent non-sooting flames and lines 108 and 110 represent sooting flames. In this example the anode was a 19 square cm steel cylinder and the cathode was a 1.5 cm long, 0.05 cm diameter nickel wire, both located 10 cm above the burner surface. It is observed that the currents obtained in the nonsooting flames reach approximately constant plateau currents over the voltage range from 100–600 as shown in FIG. 3. Sooting flames, however, show a very different probe current which is not constant over this voltage range and which is larger at larger flame equivalence ratios. Thus the basic observation upon which the technique is based is illustrated in FIG. 3, namely a very different probe current-voltage curve is observed in sooting flames as compared to nonsooting flames.

Figure 4:
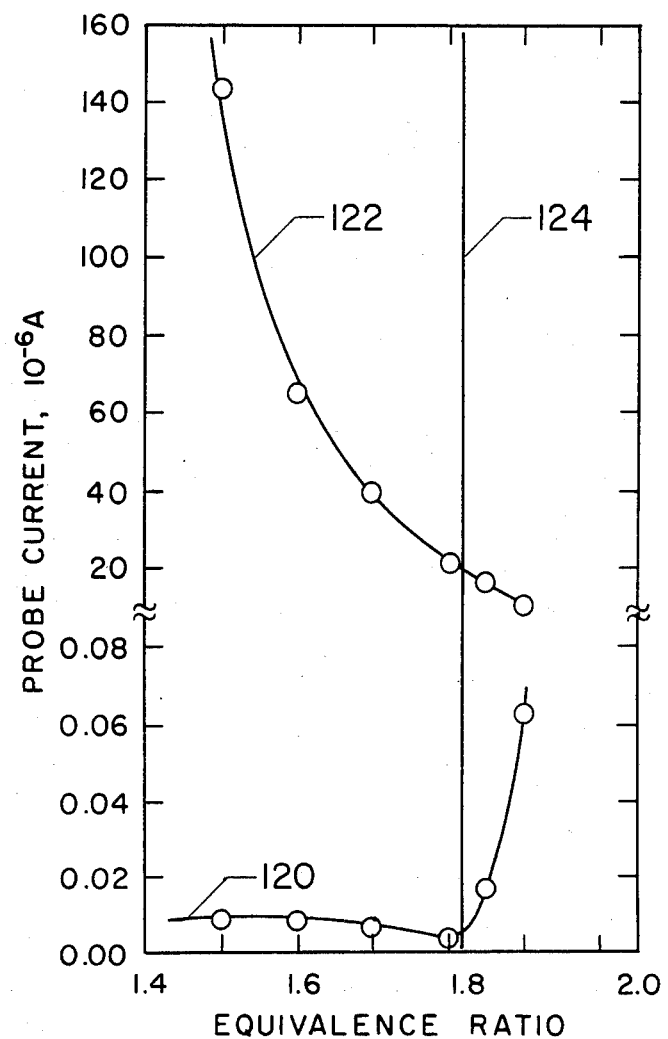
FIG. 4 shows probe currents at fixed probe voltages as a function of fuel/air equivalence ratio in a premixed flame.
Figure 5:
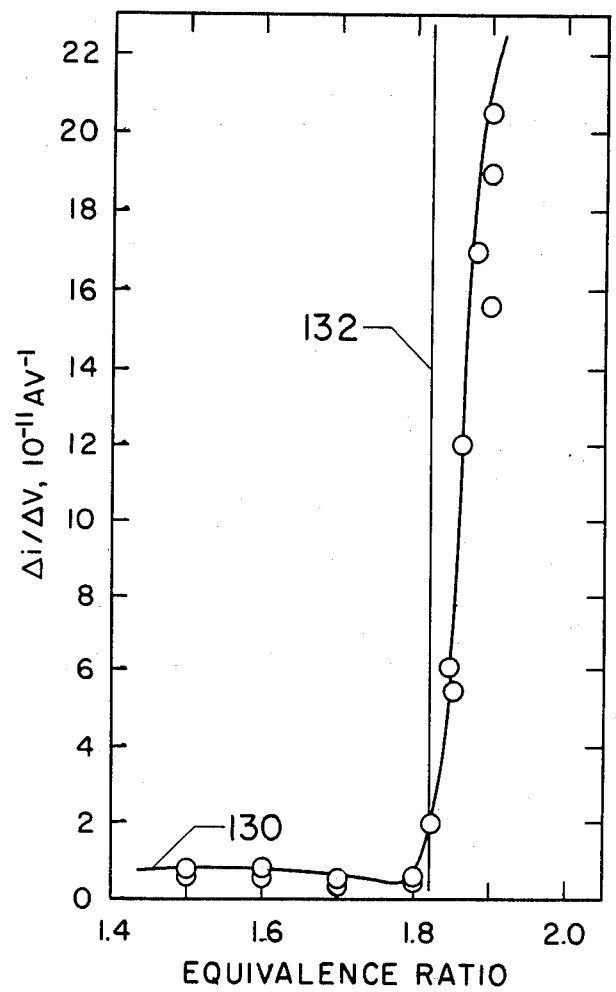
FIG. 5 shows current-voltage slopes vs. fuel/air equivalence ratio in premixed flames.
Figure 6:
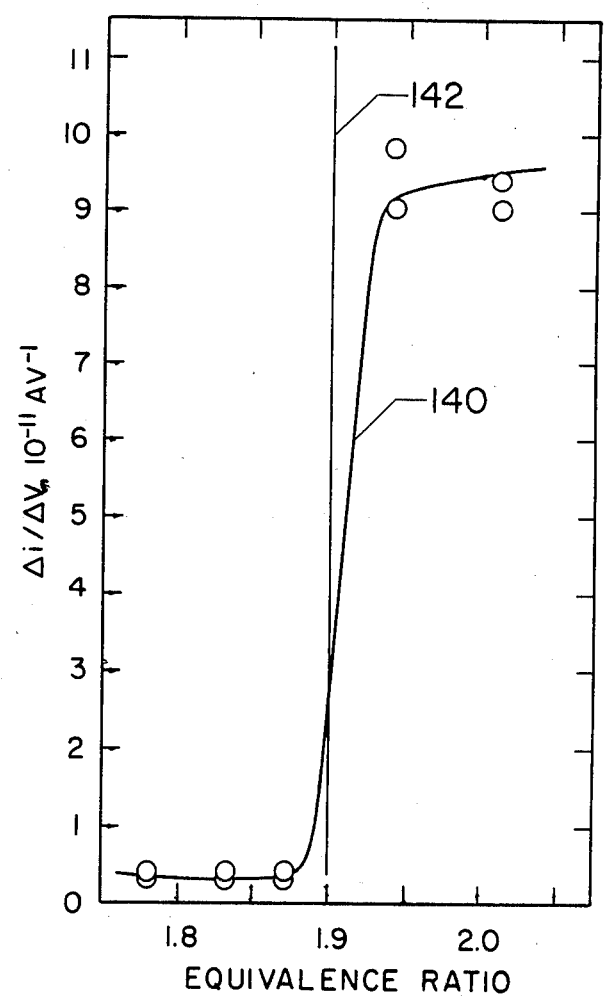
FIG. 6 shows current-voltage slopes vs. fuel/air equivalence ratios in benzene-air premixed flames.

The same data as in FIG. 3 is illustrated in FIG. 4 where the probe current at a fixed voltage of 300 V is presented vs. the flame equivalence ratio. Two curves are shown in the figure. Curve 120 was taken with the probe located 12.5 cm above the burner and curve 122 was located with the probe 1.5 cm above the flame. Line 124 represents the transition equivalence ratio. Soot is formed for flames with equivalence ratios greater than that indicated by line 124, i.e., for equivalence ratios greater than 1.82. Thus another characteristic of the probe technique is illustrated. Close to the flame the probe currents measured are very large in comparison and do not show a transition at the point of first soot formation. At further distances from the flame, shown in this example as curve 120, probe currents are much smaller and a sharp rise is noted at the threshold for soot formation. The same data shown in FIGS. 3 and 4 is also shown in FIG. 5 in the form of a current-voltage slope, specifically the change in current divided by change in voltage vs. flame fuel air equivalent ratio. Curve 130 represents the current voltage slope taken over the voltage range 200–300 Volts and line 132 represents the threshold equivalence ratio for soot formation as in FIG. 4. A sharp increase in current voltage slope is observed near the sooting threshold. FIG. 6 shows data, curve 140, similar to that shown in FIG. 5 but for a different flame system, benzene air. In this case the soot threshold is shown by the vertical line 142, located at the equivalent ratio 1.9, and the line 140 shows the current voltage slope taken from experiments which produce data similar to that shown in FIG. 3 for the propane air system. Again a large increase in current voltage slope at or near the threshold for soot formation is observed.

Figure 7:
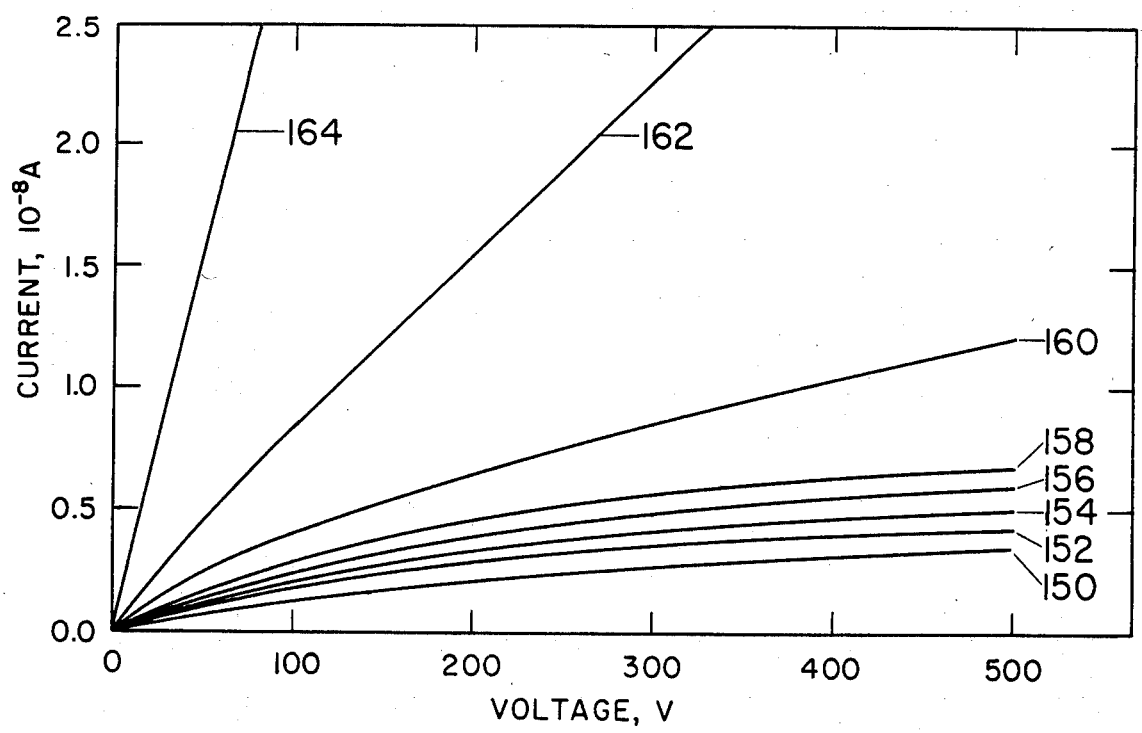
FIG. 7 shows probe current vs. probe voltage curves obtained in a diffusion flame.
Figure 8:
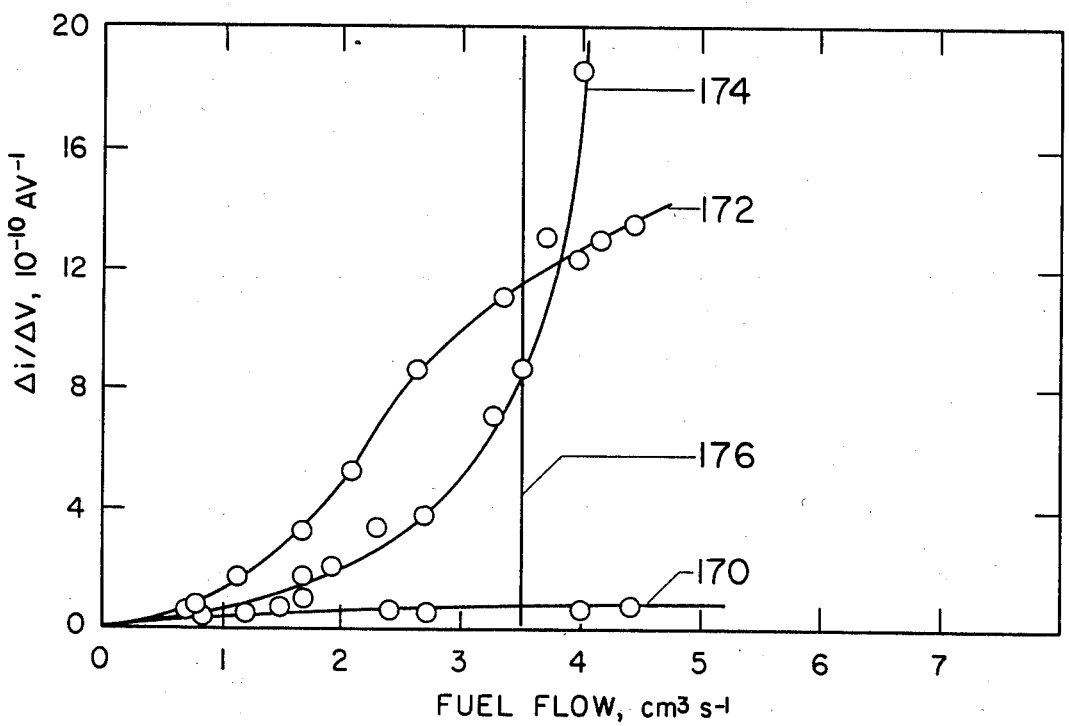
FIG. 8 shows current-voltage slopes vs. fuel flow rate in diffusion flames at three heights above the burner.

Experiments were also performed using diffusion flames instead of premixed flames in an apparatus similar to that shown in FIGS. 1 and 2 but with a different burner substituted for burner 30 in FIG. 1. FIG. 7 shows data taken from a 1,3-butadiene-air diffusion flame using a probe similar to that described in FIG. 1 and located 3.8 cm above the burner. Overventilated diffusion flames are characterized not by an equivalence ratio but by a fuel flow at constant air flow with the air flow in great excess. The lines 150–164 represent probe current obtained in flames with fuel flow rates of 0.25, 0.45, 0.73, 0.85, 1.00, 1.20, 1.47 and 2.40 $cm^3/S$ respectively. A rather sharp increase in current is observed for lines 160–164, similar to that observed in the premixed flames as shown in FIG. 3. FIG. 8 shows current-voltage slopes vs. fuel flow rates for a propane diffusion flame similar to the flame represented by data in FIG. 7. Three sets of data are shown by lines 170, 172, and 174 representing probe locations 17 cm, 2.5 cm, and 12 cm above the burner, respectively. The data represented by line 172 has been divided by 100 thus these probe currents were actually much larger than those measured at the other two probe locations. The slopes were taken from data between voltages of 300 and 400 V. At 17 cm above the burner, line 170, little probe current was measured. At 2.5 cm above the burner, line 172 a large quantity of current was measured which showed no transition at the point where the flame first emitted smoke, represented by the line 176 for a fuel flow of 3.5 $cm^3/S$. However, when the probe was located at 12 cm above the burner an increase characteristic of the smoke emission, line 174 was obtained. The transmition at the smoke threshold, however, was not as abrupt as in the previous examples.

Figure 9:
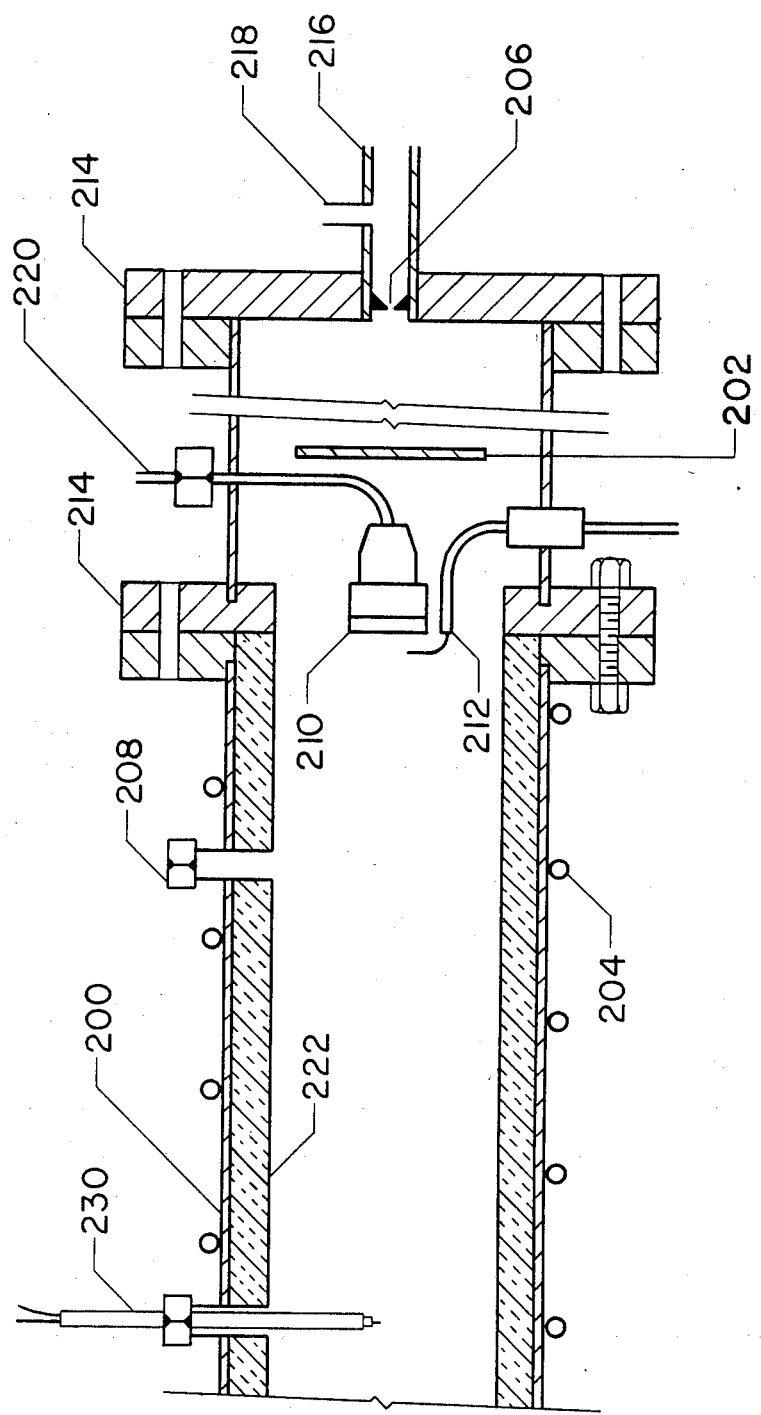
FIG. 9 shows an alternative embodiment of the invention in a turbulent combustion apparatus.
Figure 10A:
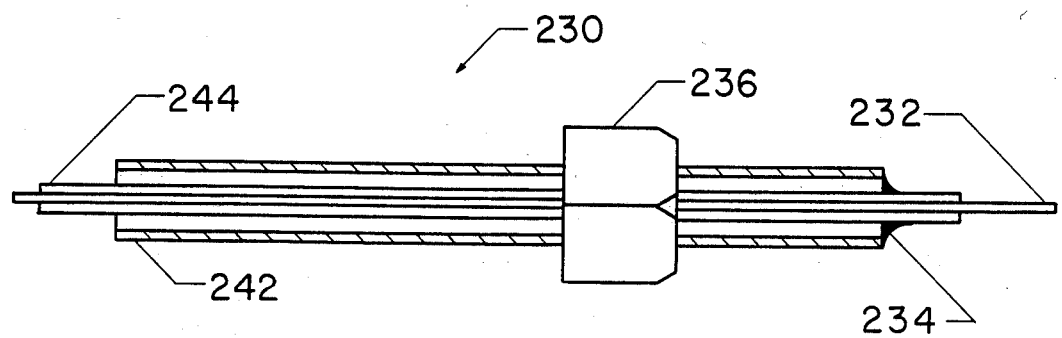
FIGS. 10a, 10b, and 10c show alternate embodiments of the probe construction used in the FIG. 9 combustion apparatus.
Figure 10B:
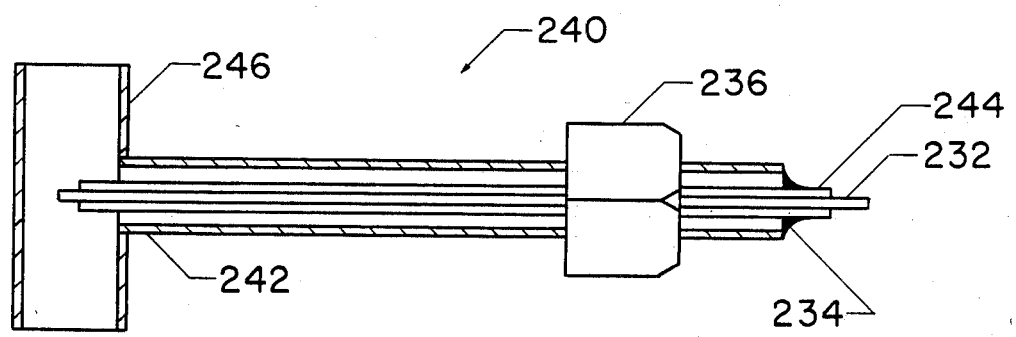
Figure 10C:
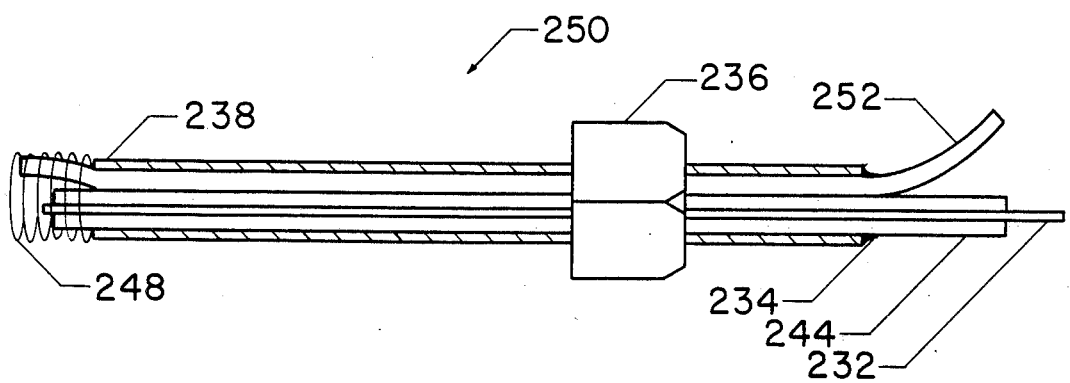

FIG. 9 shows another combustion apparatus in which the probe technique was tested. The apparatus, which will be referred to as the turbulent flow tube combustor, basically contains a flowing air stream in which liquid fuel is atomized and burned in a highly turbulent flame. Downstream of this flame the probe apparatus was tested. The turbulent flow tube combustor is constructed from two sections of 10.2 cm i.d. brass tube, 200, mated together and closed at the end by brass flanges, 214. Air enters the combustor through tube 216 at a rate controlled by orifice 206 and at a pressure measured through the tube 218. The first section of the combustor is approximately 30 cm in length amd contains a disk, 202, to induce turbulence which mixes the air and the sprayed fuel. Fuel enters the combustor through tube 220 and is sprayed from nozzle 210. The flame is initially ignited using an electrical spark apparatus 212. The combustor tube downstream of the fuel nozzle contains a lining 222 of refractory alumina insulation with an inner diameter of 7.6 cm. The brass tube in this section is water cooled at the outer wall through tubes 204. Eight fittings were installed in the combustor wall beginning 7.5 cm downstream of the fuel nozzle. These ports allow 0.6 cm diam probes to be inserted through the wall into the combustion flow at various distances downstream to measure temperatures, currents, and soot concentrations. A typical probe is shown in FIG. 9 as item 230. Details of probe configurations tested in the turbulent flow tube combustor are shown in FIGS. 10a, 10b, and 10c. All three are essentially cylindrical tubes which can be inserted through the ports in the combustor wall and sealed using fitting nut 236. The probes in FIGS. 10a and 10b use a 0.6 cm diameter stainless steel tube, 242, as the outer support. Inside the tube is located an alumina tube, 244 and contained inside this alumina tube is the probe wire which forms the cathode of the probe. The concentric tubes and wire were sealed against flowing gases using common epoxy adhesive 234. The anode for the probes 230 and 240 were in each case the whole combustor body operated at ground potential. The probe in FIG. 10b has another section of 0.6 cm diam stainless steel tube, 246, welded at its end perpendicular to the tube 242. Thus the flame gases contained inside the tube 246 are exposed to the end of probe wire 232 and a unique volume of flame gases is defined from which the electrical probe current is obtained. The probe in FIG. 10c, 250, is slightly different in construction. The basic support for the tube consist of a 0.6 cm diameter alumina tube 238 containing another smaller alumina tube 244. The probe cathode wire 232 is in the center of these concentric tubes and another similar wire for anode 252 is in the annular region. An epoxy seal 234 prevents the escape of flame gases. A small wire is wrapped around the end of the probe anode 248 which defines the unique volume from which ion current can be obtained. This construction allows flame gases to flow through this region unimpeded and is characterized by smaller volume than the probe 240.

Figure 11:
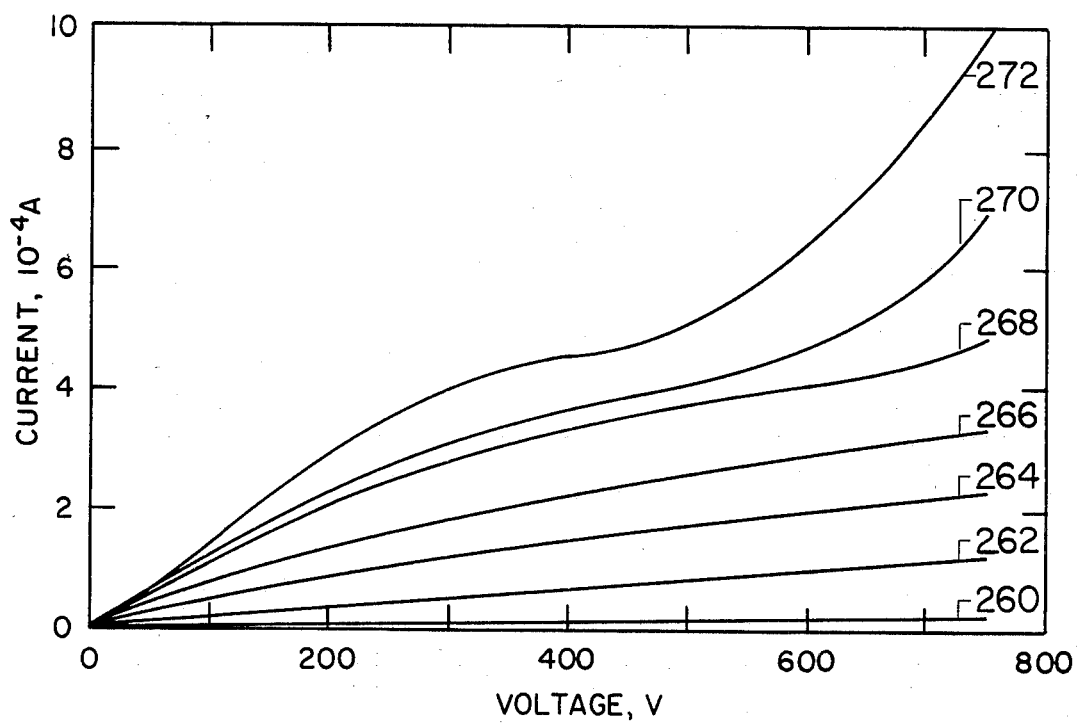
FIG. 11 shows current vs. voltage curves obtained in the turbulent combustion apparatus.
Figure 12:
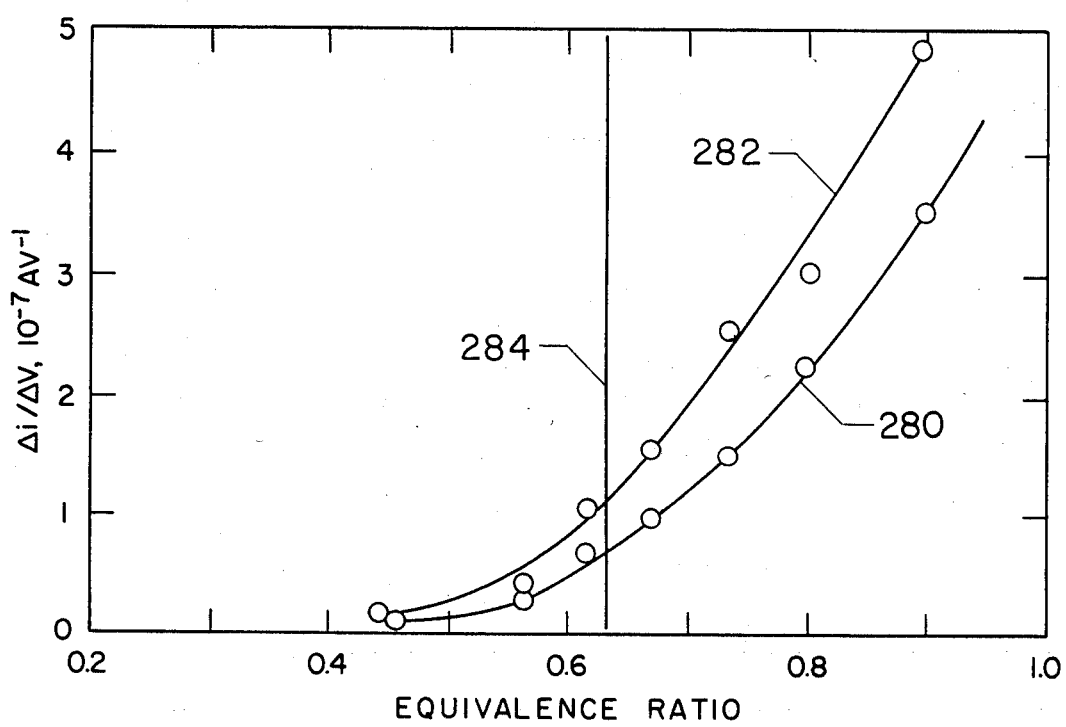
FIG. 12 shows current-voltage slopes vs. fuel/air equivalence ratio in the turbulent combustion apparatus.

All three probes were tested in the turbulent flow tube combustor shown in FIG. 9. Probe currents obtained using the probe 240 shown in FIG. 10b as a function of voltage are shown in FIG. 11. The curves 260–272 represent various fuel to air equivalence ratios for operation of the combustor, specifically equivalence ratios of 0.45, 0.57, 0.62, 0.67, 0.73, 0.80 and 0.89 respectively. The turbulent flow tube combustor does not exhibit a sharp threshold for soot production. At the smaller fuel/air equivalence ratios little or no soot is produced in the exhaust. At the higher fuel/air equivalence ratios a large amount of visible smoke is emitted in the exhaust but the transition from one operating condition to the other is gradual. The current voltage curves shown in FIG. 11 reflect this gradual transition from non-sooting to sooting condition. The slopes of the current-voltage curves are shown in FIG. 12 vs. fuel-/air equivalence for the data shown in FIG. 11. The line 284 represents the approximate transition between sooting and non-sooting combustor operation. The two other lines represent slopes taken between 100 and 200 Volts for line 282 and 300 and 500 Volts for line 280. The data presented in both FIG. 11 and FIG. 12 are flames of a mixture of 75% toluene and 25% tetralin for the fuel. Thus FIG. 12 demonstrates that the probe is sensitive to the increases soot formation in the turbulent flow tube combustor.

Figure 13:
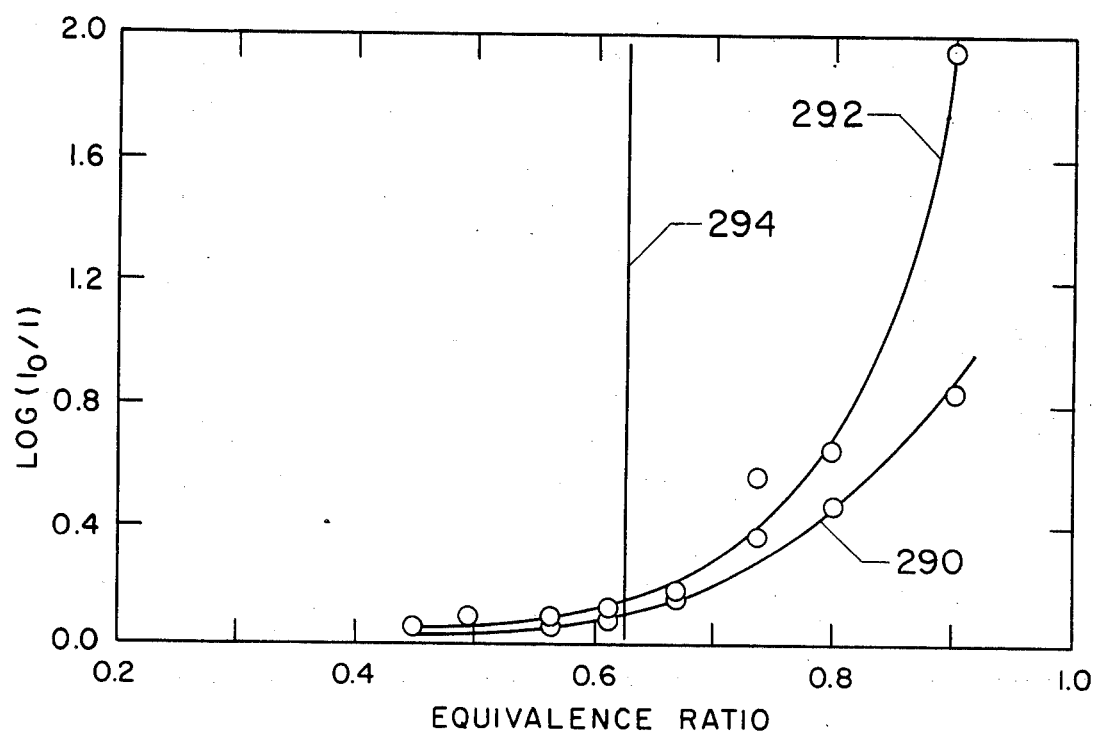
FIG. 13 shows measurements of relative soot concentrations as a function of fuel/air equivalence ratio in the turbulent combustion apparatus.

To better define the quantity of soot produced in the turbulent flow tube combustor at different fuel/air equivalence ratios, experiments were performed to measure the relative quantity of soot in the exhaust gases as a function of operating conditions. These experiments were performed by passing some of the exhaust gases through a white filter paper which collected the soot. The relative darkness of the soot deposited on the filter paper was used as a measurement of the quantity of soot in the flame gases. FIG. 13 shows data on the opacity of the filter paper, that is, the logarithm of the ratio of the light transmitted through a clean filter paper divided by the light transmitted through the filter paper containing soot. This filter paper opacity is seen in the figure to increase with increasing fuel/air equivalence ratio. Two sets of data are shown by curves 290 and 292, both taken 97 cm downstream from the fuel nozzle. Vertical line 294 represents an approximate judgment of the threshold for soot formation in this combustion, defined as the point where the filter paper opacity reached twixe its approximately constant value from nonsmoking flames. Thus for this fuel a soot threshold was measured at 0.63 equivalence ratio which was used to compare with the probe results.

Figure 14:
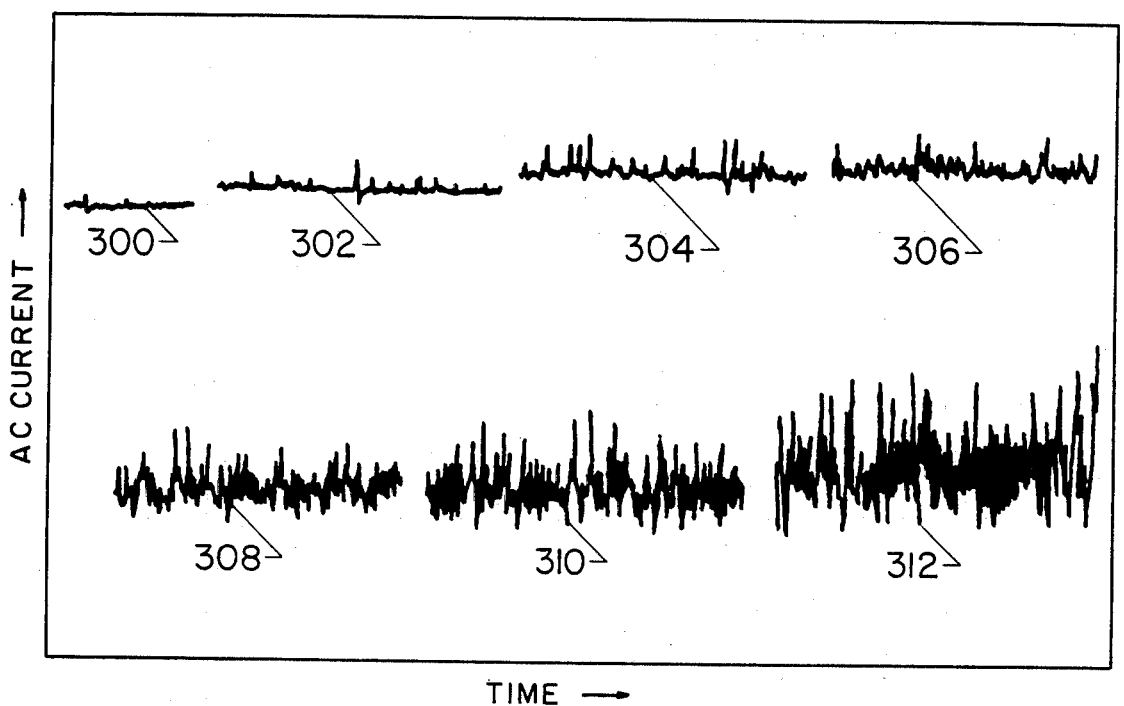
FIG. 14 shows a.c. probe currents obtained at several fuel/air equivalence ratios in the turbulent combustion apparatus.
Figure 15:
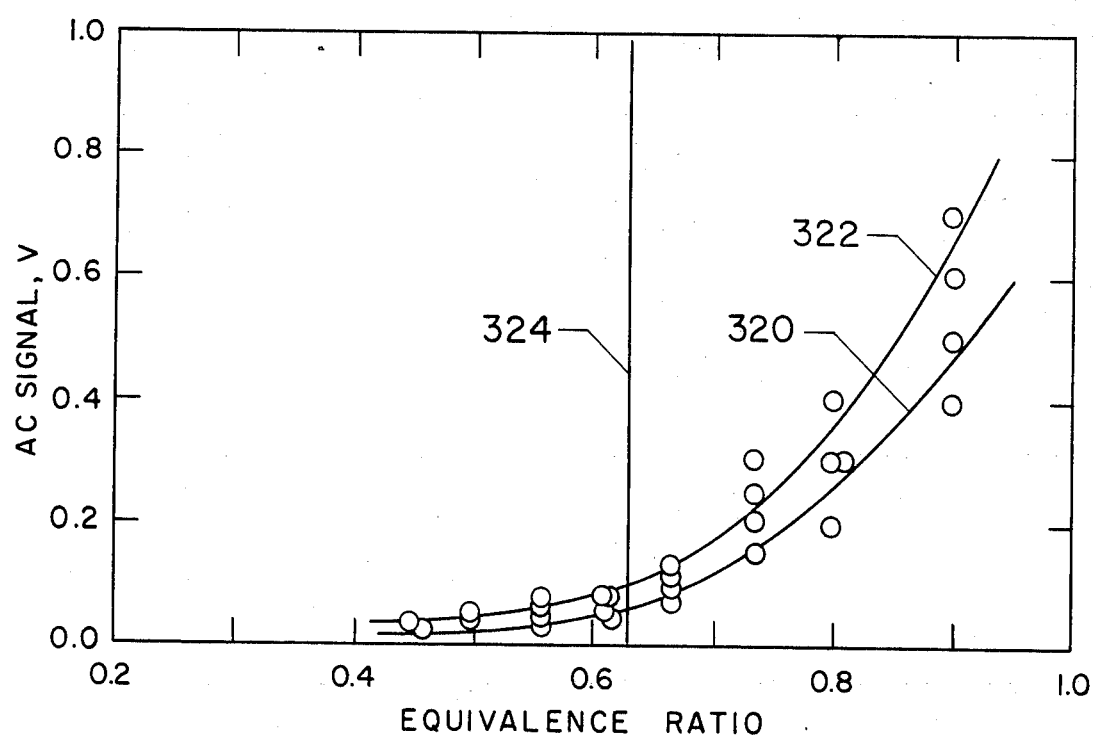
FIG. 15 shows the average a.c. probe voltage vs. fuel/air equivalence ratio obtained in the turbulent combustion apparatus.

FIG. 14 shows another kind of data taken in the turbulent flow tube combustor using a probe as shown in FIG. 10c. The FIG. 14 data is the a.c. noise fluctuations on the probe current as a function of fuel/air equivalence ratio, all data taken with 500 Volts applied to the probe and located at 67 cm downstream from the nozzle. Lines 300-312 represent fuel/air equivalence ratios of 0.45, 0.56, 0.63, 0.67, 0.74, 0.80, and 0.90 respectively. From FIG. 13 the approximate soot threshold was determined to be an equivalence ratio of 0.63. It can be seen in FIG. 14 that the a.c. noise signal increases as a function of equivalence ratio. A measurement of this noise intensity is shown in FIG. 15 where the root mean squared value of the a.c. signal is polotted vs. equivalence ratio. Data is shown for two probe voltages, 500 Volts for curve 320 and 1000 Volts for curve 322. This a.c. noise probe signal is also sensitive to the increased amount of soot produced in the turbulent flow tube combustor.

FIGS. 1-17 show a preferred embodiment of the saturation current incipient soot detector invention, data taken in the laboratory using this preferred embodiment, data taken using different fuels and flame systems, and data and apparatus consisting of a third general type of flame with the latter flame probably more like practical combustors. In a combustor where operation is characterized by a sharp threshold onset of soot formation and with the probe located sufficiently away from the chemi-ion production region, the probe technique is sensitive to early appearance of soot in the exhaust. This probe technique has the advantage of not requiring windows through the combustor wall which are difficult to keep clean and it is simple in construction and operation. For combustion systems where there is a gradual transition from non-sooting to sooting the probe has been shown to give a measurement of the soot production in these cases, also showing a gradual transition in character. It is envisioned, therefore, that this probe could be used in either situation, requiring a threshold level to be detected when the transition is gradual. Various electronic methods of extracting information from the probe current-voltage profiles are obvious to one skilled in these arts. A ratio or slope measurement of the current voltage profile or a current measurement at a fixed potential could be used. The a.c. noise current generated on the probe signal could also be used or the probe voltage could be switched rapidly to higher and lower voltages and the currents obtained at each voltage compared by a simple circuit or a small computer.

Figure 16:
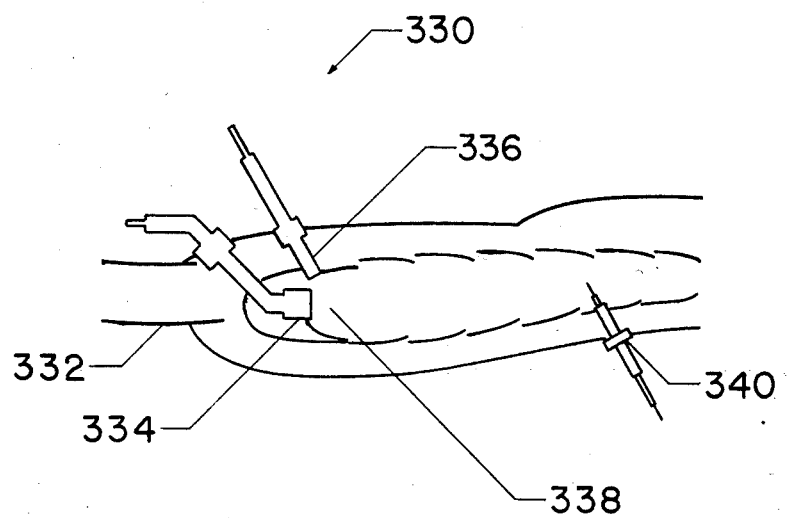
FIG. 16 illustrates the invention employed to detect soot in a turbojet engine combustor.

The applications of this invention are relatively broad. One example of an application of this invention would be in a gas turbine engine where the primary combustion zone is relatively fuel rich and excess air is added in the downstream sections of a combustor. A typical turbojet engine combustor system 330 is illustrated in FIG. 16. Air is introduced through air inlet 332 and mixes with fuel from nozzle 334. Ignitor 336 causes the mixture to burn in flame zone 338. A soot probe 340 according to the teachings of this invention is located in a region of flame zone 338 where soot might occur. Smoke produced in the initial fuel rich combustion often is not oxidized in the later sections of the combustor because the temperature is much lower. The electrostatic probe 340 could be used to adjust the primary zone fuel air ratio and control it so as to prevent smoke emissions from the engine. It should be possible to operate this primary combustion zone fuel rich, near the smoke threshold but without exceeding that threshold. These conditions are desirable in some instances to operate the combustor with a lower flame temperature in order to reduce the production of oxides of nitrogen.

Figure 17:
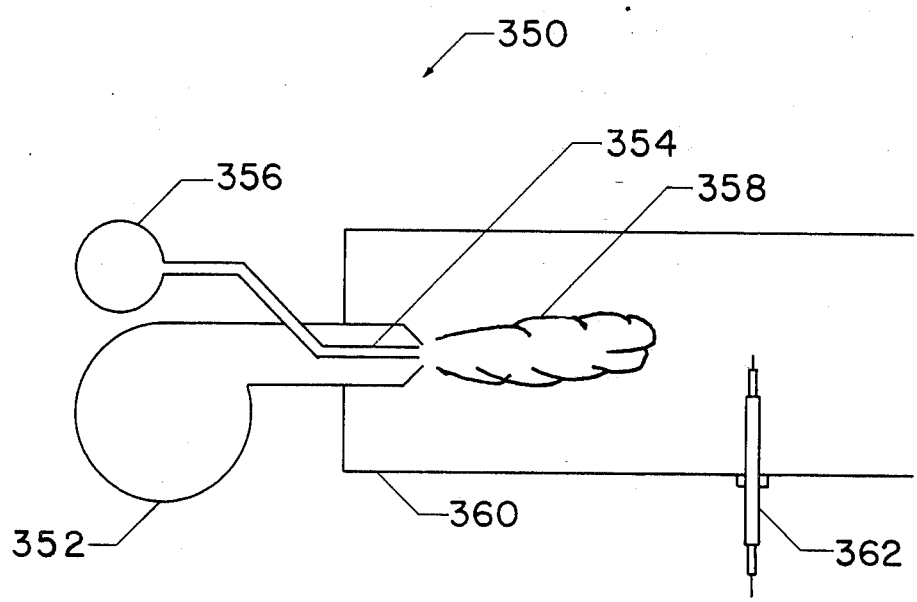
FIG. 17 illustrates the invention employed to detect soot in an oil or gas furnace.

Another application would be in the exhaust of a gas or oil fired boiler combustor where smoke emissions are undesirable. It would be possible to install the probe in the hot exhaust gases but located away from the luminous flame zone. A typical oil or gas fired furnace system 350 is illustrated in FIG. 17. Air is brought into the system by blower 352. Oil or gas from a fuel supply tank 356 is forced through nozzle 354. The fuel/air combination produces a turbulent flame 358 which is contained by furnace wall 360. A soot probe 362 is located in the region of the furnace where soot is likely to form.

The invention just described finds special applications in detecting thresholds for smoke formation in combustion exhausts. It will be appreciated by those of ordinary skill in the art that this invention could be used to detect the presence of other particles which can be thermally ionized at high temperatures in a manner similar to that used to detect soot.

We claim:

1. A detection apparatus for determining the onset of sooting conditions in a flame having a flame front, said detection apparatus comprising:
   probe means for insertion down-stream of said flame front, said probe means including a negative electrode and a positive electrode;
   a voltage supply means connected to said electrodes for applying a variable voltage across said electrodes; and,
   detecting means for detecting the change from a substantially chemi-ionization saturation current condition to a substantially thermal ionization non-saturation current condition across said electrodes, wherein said detecting means is sufficiently sensitive to detect the substantial change in the current voltage relationship which identifies the transition from a substantially chemi-ionization saturation current condition to a substantially thermal ionization non-saturation current condition at the onset of soot formation.

2. The apparatus of claim 1 wherein said detecting means comprises:
   a sensitive measuring means for measuring the current flow across said electrodes; and,
   a display means for displaying the current across said electrodes.

3. The apparatus of claim 1 wherein said detecting means comprises:
   a means for meassuring the slope of the current vs. voltage characteristic of the gas between the electrodes.

4. The apparatus of claim 1 wherein said negative electrode is smaller than said positive electrode.

5. The apparatus of claim 1 wherein said voltage supply means comprises a variable direct current voltage supply.

6. The apparatus of claim 1 wherein said flame is the flame produced by an oil burner.

7. The apparatus of claim 1 wherein said flame is the flame produced by a gas burner.

8. The apparatus of claim 1 wherein said flame is the flame produced by a jet engine.

9. A method for detecting the early appearance of soot particles in flame gases beyond a flame front, said method comprising the steps of:
   placing a probe down-stream of said flame front, said probe comprising a positive and a negative electrode;

applying a variable voltage across said electrodes; and, monitoring the current across said electrodes for the significant change in current vs. voltage characteristics that accompanies the onset of soot formation in said flame gases as said current changes from substantially chemi-ionization saturation current conditions to substantially thermal ionization non-saturation current conditions.

10. The method of claim 9 wherein said monitoring step monitors for a significant increase in current across said electrodes as said current changes from said chemi-ionization saturation conditions to said thermal-ionization non-saturation current conditions.

11. The method of claim 9 wherein said monitoring step monitors for a significant increase in the current voltage slope characteristic as the fuel air ratio is changed.

12. The method of claim 9 wherein said monitoring step comprises the steps of:
measuring the change from a saturation current to a non-saturation current across said electrodes; and,
determining the point of substantial change in current vs. voltage characteristics indicating the onset of sooting conditions.

13. The method of claim 9 wherein said flame is a laminar pre-mixed flame.

14. The method of claim 9 wherein said flame is a laminar diffusion flame.

15. The method of claim 9 wherein said flame is a turbulent pre-mixed flame.

16. The method of claim 9 wherein said flame is a turbulent diffusion flame.

17. The method of claim 9 wherein said flame is a high temperature gas flow.

18. The method of claim 9 wherein said flame is a flame found in an oil burner.

19. The method of claim 9 wherein said flame is a flame found in a gas burner.

20. The method of claim 9 wherein said flame is a flame found in a jet engine.

21. A method of detecting the onset of sooting conditions in a flame comprising the steps of:
positioning at least one negatively charged electrode of a pair of electrodes in the region of said flame where soot forms, and,
detecting the point at which the current across said electrodes changes from a substantially chemi-ionization saturation current to a substantially thermal ionization non-saturation current,
whereby the detection of said point of change is indicative of incipient soot formtion.

* * * * *